United States Patent
Woffinden et al.

(10) Patent No.: US 6,264,692 B1
(45) Date of Patent: *Jul. 24, 2001

(54) OPHTHALMIC LENS WITH REDUCED EDGE GLARE AND METHOD OF MAKING

(75) Inventors: George J. Woffinden, Covina; Michael Lee Fledderjohann, Phelan, both of CA (US)

(73) Assignee: Bausch & Lomb Surgical, Inc., Claremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/067,307

(22) Filed: Apr. 27, 1998

Related U.S. Application Data (62) Division of application No. 08/669,645, filed on Jun. 24, 1996, now Pat. No. 5,755,786, which is a continuation of application No. 08/198,018, filed on Feb. 17, 1994, now abandoned, which is a continuation-in-part of application No. 08/112,824, filed on Aug. 26, 1993, now abandoned, which is a continuation of application No. 07/952,388, filed on Sep. 28, 1992, now abandoned.

(51) Int. Cl.$^7$ ........................................ A61F 2/16
(52) U.S. Cl. .............................................. 623/6.17
(58) Field of Search .................... 623/4, 5, 6, 6.17, 623/5.11, 5.13–5.15, 6.11, 6.4, 6.48

(56) References Cited

U.S. PATENT DOCUMENTS

| | | |
|---|---|---|
| 2,224,793 | 12/1940 | Malcom . |
| 3,228,741 | 1/1966 | Becker . |
| 3,578,850 | 5/1971 | Grant . |
| 4,103,992 * | 8/1978 | Breger et al. .................... 351/160 R |
| 4,192,022 * | 3/1980 | LaHaye . |
| 4,298,994 | 11/1981 | Clayman . |
| 4,449,257 | 5/1984 | Koeniger . |
| 4,565,198 | 1/1986 | Koeniger . |
| 4,596,578 | 6/1986 | Kelman . |
| 4,704,122 | 11/1987 | Portnoy . |
| 4,743,254 | 5/1988 | Davenport . |
| 4,755,182 | 7/1988 | Holmes . |
| 4,781,717 * | 11/1988 | Grendahl . |
| 4,808,181 | 2/1989 | Kelman . |
| 4,989,967 * | 2/1991 | Matsuda .............................. 351/165 |
| 5,009,497 | 4/1991 | Cohen . |
| 5,053,171 | 10/1991 | Portney et al. . |

(List continued on next page.)

FOREIGN PATENT DOCUMENTS

| | | |
|---|---|---|
| 0276331 | 12/1956 | (EP) . |
| 0190056 | 1/1986 | (EP) . |
| 0419740 | 9/1989 | (EP) . |
| 0366356 | 10/1989 | (EP) . |
| 2180759 | 4/1987 | (GB) . |
| WO92/17134 | 10/1992 | (WO) . |

OTHER PUBLICATIONS

Artificial eye lens—p.32 1990 Derwent Publications Ltd. 90–244636/32—SU 1537 24–A.

Hypermetropic epikeratoplasty corneal transplant—p. 32 1992 Derwent Publications Ltd. 92–112735/14—SU 1660–694–A.

Primary Examiner—David H. Willse
(74) Attorney, Agent, or Firm—Rita D. Vacca (57) ABSTRACT

An opthalmic lens and a method of making is disclosed. The lens has a one-piece lens body with an integral edge surface. The edge surface reflects visible light which contacts the edge surface away from the retina of the patient. The edge surface has beveled portions or a curve of a convex form. The bevels or convex form are displayed on the edge by milling with a milling cutter having a shape matching that desired on the edge. This lens design reduces glare seen by the patient caused when incident light contacts the edge surface and is undesirably reflected onto the retina.

11 Claims, 6 Drawing Sheets

U.S. PATENT DOCUMENTS

| | | |
|---|---|---|
| 5,104,590 | 4/1992 | Blake . |
| 5,152,786 * | 10/1992 | Hanna . |
| 5,152,787 | 10/1992 | Hambien . |
| 5,156,622 | 10/1992 | Thompson . |
| 5,171,320 | 12/1992 | Nishi . |
| 5,192,318 | 3/1993 | Schneider et al. . |
| 5,203,790 * | 4/1993 | McDonald .......................... 623/6.17 |
| 5,204,160 | 4/1993 | Rouser . |
| 5,266,074 | 11/1993 | Nishi et al. . |
| 5,270,744 | 12/1993 | Portney . |
| 5,384,606 | 1/1995 | Koch et al. . |
| 5,405,385 | 4/1995 | Heimke et al. . |
| 5,425,759 | 6/1995 | McDonald . |
| 5,549,670 | 8/1996 | Young et al. . |
| 5,578,080 * | 11/1996 | McDonald .......................... 623/6.17 |

* cited by examiner

OPHTHALMIC LENS WITH REDUCED EDGE GLARE AND METHOD OF MAKING

This application is a divisional of application Ser. No. 08/669,645, filed Jun. 24, 1996, now U.S. Pat. No. 5,755, 786, which is a continuation of application Ser. No. 08/198, 018, filed Feb. 17, 1994, now abandoned, which is a continuation-in-part of application Ser. No. 08/112,824, filed Aug. 26, 1993, now abandoned, which is a continuation of application Ser. No. 07/952,388, filed Sep. 28, 1992, now abandoned.

BACKGROUND OF THE INVENTION

This invention relates to an opthalmic lens which is designed to minimize the amount of visible light reflected onto the retina from the edges of the lenses. More specifically, it relates to an opthalmic lenses, especially an intraocular lens, which has a lens body with an edge surface designed to reflect incident light on the edge surface away from the retina.

Conventional intraocular lenses typically have flat edges that, under certain conditions, can reflect incident light onto the retina to produce unwanted optical images, such as halos, rings, or arcs (commonly referred to as "glare"). Typically, the images occur when the pupil dilates large enough to expose, or nearly expose, the edge surface of the lens. These conditions occur at night or in dim light. For example, the unwanted images can be produced while driving at night by light rays from headlights of oncoming cars as the rays reflect or scatter from the exposed edges of the lens.

The problem of glare has worsened for intraocular lenses which have been specifically designed for small incision surgery. Iz lenses for small incision surgery may have a lens body which is round or oval, but the diameter of the lens body is smaller than that of a lens designed for conventional surgery. Therefore, the edges of these small diameter lenses are more often exposed to incident light.

More commonly, intraocular lenses for small incision surgery have an oval shape. These oval shaped lenses are referred to as "ovoid" lenses, and such lenses are described in Clayman's patent, U.S. Pat. No. 4,298,244. Because of the method of manufacture of these ovoid lenses, the ovoid has thicker edges on the small diameter sizes of the lens body. It is therefore particularly susceptible to reflections and glare, because the thicker edges provide more surface area for reflections and therefore amplify these problems.

The popularity of small incision surgery is increasing and the ovoid has become the lens of choice for many small incision surgeons. Edge glare is one of the main drawbacks of ox lenses. Popularity with these lenses will continue to grow if the glare problem can be controlled.

Unfortunately, lens designs which have attempted to deal with the glare problem have been far from practical or efficient in dealing with this problem. For example, U.S. Pat. No. 4,596,578 discloses an intraocular lens having a lens body and a deformable positioning member for fixing the position of the lens body in the anterior chamber of the eye. The lens body and the positioning member are separately inserted into the eye, and then connected together in the eye to form the lens. A portion of the positioning member covers the periphery of the lens body, and this portion may be shaped so that light rays contacting the periphery of the lens body are deflected away from the retina. While this lens design may work in theory to help minimize glare, it represents a cumbersome attempt to deal with this problem. It is clearly undesirable from a surgeon's point of view to have to first insert the lens body of the intraocular lens, and then afterwards insert a positioning member which must then be connected to the lens body.

Other attempts have been made to minimize the effect of glare in intraocular lenses. U.S. Pat. No. 4,781,717 discloses an intraocular lens having a lens body and an integrally attached rim surrounding the lens body which covers the edge of the lens body. Reduction in "edge effect" and glare can be achieved according to this patent by adding a different color or using a different material for the rim. U.S. Pat. No. 4,743,254 describes an intraocular lens having a lens body and a deformable glare attachment. The glare attachment and lens body form a circle, and the glare attachment can be envisioned as "flaps" which fold down so that the intraocular lens can be inserted through a small incision in the eye. The glare attachment is desirably opaque to reduce the transmission of light through this section in comparison to the optical lens body. Once again, while these two approaches may appear to work in their to reduce glare, the lens designs are difficult to fabricate and create unnecessary complications for the surgeon when the lens is to be implanted into the eye. Additionally, these lens designs require incorporating a coloring agent or a different component into the lens composition, which further complicates the manufacturing process.

Another interesting design to minimize glare in an intraocular lens can be found in U.S. Pat. No. 4,755,182. This patent discloses an intraocular lens having positioning holes displayed on the periphery of the lens body to aid the surgeon in manipulating and inserting the intraocular lens into the eye. The positioning holes are drilled only partially through the lens body, and the interior surface of the hole is not polished. These design features for the positioning holes reduce glare significantly. However, there is no discussion relating to any means for reducing glare caused by incident light contacting the edge surface of the lens body of the intraocular lens.

While the discussion here has been limited primarily to intraocular lenses, the problem of edge glare is also inherent for other opthalmic lenes. Although there is a major effort to design smaller intraocular lenses for small incision surgery, which has led to burgeoning edge glare problems, the reader should not overlook the fact that these problems also occur with other ophthalmic lens designs, particularly lens design for contact lenses and spectacles.

In view of the pervasive nature of this edge glare problem for all types of opthalmic lenses, it would be highly desirable to form an opthalmic lens which is simple in design, and yet alleviates the problem of edge glare. More specifically, the opthalmic community needs a lens with a simple one-piece design for the lens body of the lens which has an edge surface characterized in such a way that it significantly reduces or essentially eliminates the creation of unwanted glare.

SUMMARY OF THE INVENTION

The invention is an opthalmic lens. The lens comprises a one-piece lens body for focusing visible light on the retina of a patient. The lens body has an integral edge surface which defines the circumference of the lens body. The integral edge surface includes means displayed on this surface for reflecting visible light which contacts the edge surface away from the retina of the patient.

The opthalmic lens of this invention is simple in design. It significantly reduces or eliminates patient glare caused by incident light contacting the edge surface of the lens, and then reflecting onto the retina. The lens does not require fabrication from two or more separate pieces to form the lens body, and the surgeon is not required to implant separately connectable components into the patient's eye. Nothing is needed to cover the edge surface of the lens body to minimize or eliminate glare caused by light contacting the edge surface. Additionally, the peripheral portion of the lens body, including the edge surface, does not need to be composed of a different material from that of the primary lens optic. For example, it is unnecessary to incorporate into the material defining the periphery of the lens body a component or combination of components which are intended to reduce the transmission of light through these peripheral regions.

The lens comprises a lens body having two optical surfaces joined by a third, integral edge surface having a beveled portion or being convexly curved such that light incident upon the edge surface is reflected away from the retina of the eye.

DETAILED DESCRIPTION OF THE PREFERRED EMBODIMENT

For the purpose of describing this invention, an opthalmic lens is any lens for the eye which improves vision, provides therapy, or enhances or modifies appearance. Such lenses include, but are not limited to, intraocular lenses, contact lenses, corneal inlay lenses, corneal bandage lenses, and spectacles. Preferably, the opthalmic lens is designed for placement on the cornea or in the eye. The preferred lenses are intraocular lenses and contact lenses. The most preferred lens is an intraocular lens. An intraocular lens is an artificial lens which is implanted in the eye following cataract surgery when the natural lens of the eye is removed.

As defined in this specification, the lens body of the opthalmic lens refers solely to the optical lens portion of the lens. Therefore, the opthalmic lens of this invention would not exclude, for example, an intraocular lens conventionally known as a "three-piece lens", which has a lens body to which is attached two filamentary haptics, so long as this three-piece lens has a one-piece lens body.

Figure 1:
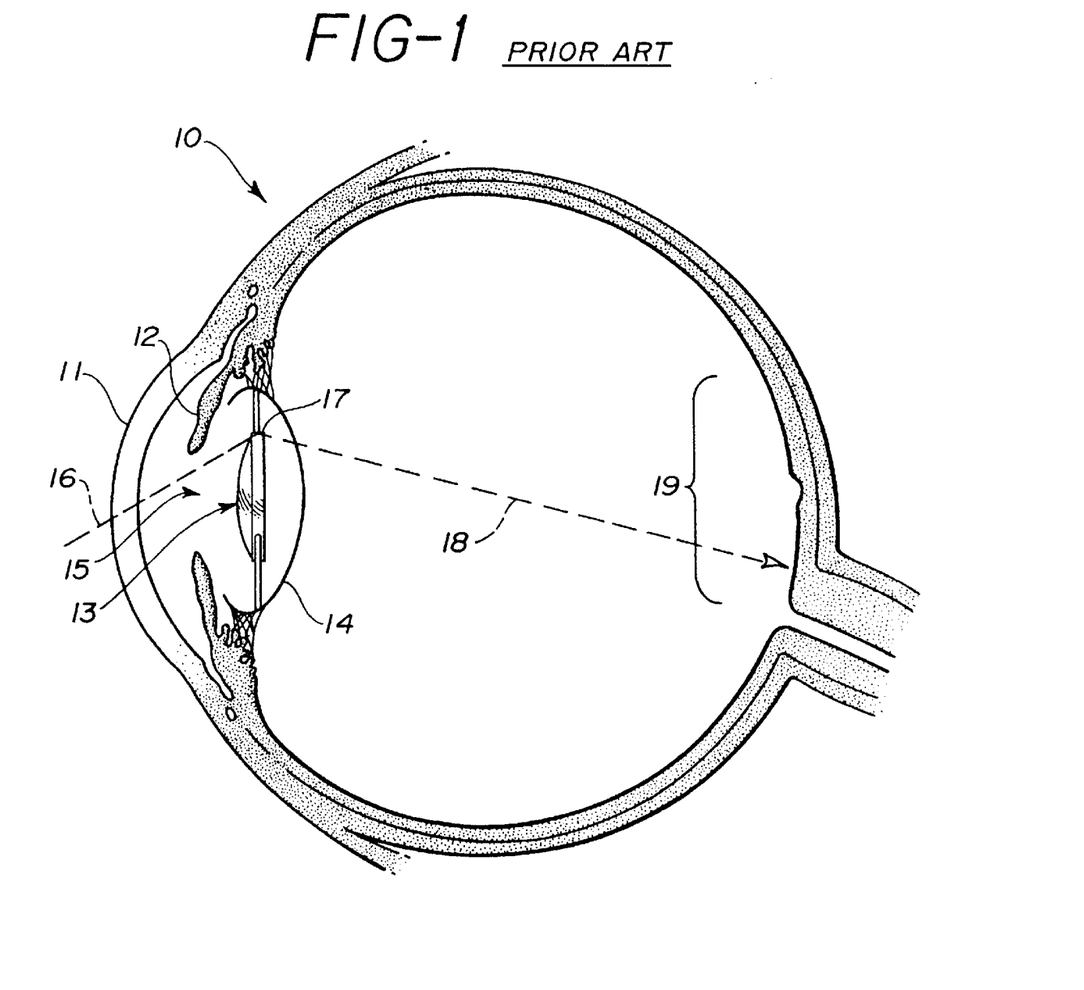
FIG. 1 is a schematic cross-sectional view of a human eye showing the pathway of an incident beam of light reflected from the edge of the lens body of a conventional intraocular lens implanted in the human eye.

To illustrate the difficulties which this invention solves in a simple manner, the pathway of an incident beam of light across the edge of a conventional, implanted intraocular lens is represented in FIG. 1. There is shown at FIG. 1 a human eye 10, which includes the cornea 11 at the exterior of the eye, and the iris 12. An intraocular lens 13, such as a posterior chamber lens, is implanted in the posterior capsule 14 of the eye following cataract surgery to provide proper focusing of light which enters the eye through the pupil 15. An incident beam of light 16 entering the eye through the pupil may strike the edge 17 of the lens body of the intraocular lens. When the edge surface is conventionally flat or rounded commonly used in the prior art, the light beam 18 reflects off of the edge surface toward the back of the eye posteriorly until it impinges upon the active retinal region 19 of the eye. This reflection causes glare, which is any unwanted optical image formed on the retina of the eye. In a similar manner, unwanted glare can be formed by edge reflections from other opthalmic lenses, most notably contact lenses and spectacles.

Figure 2A:
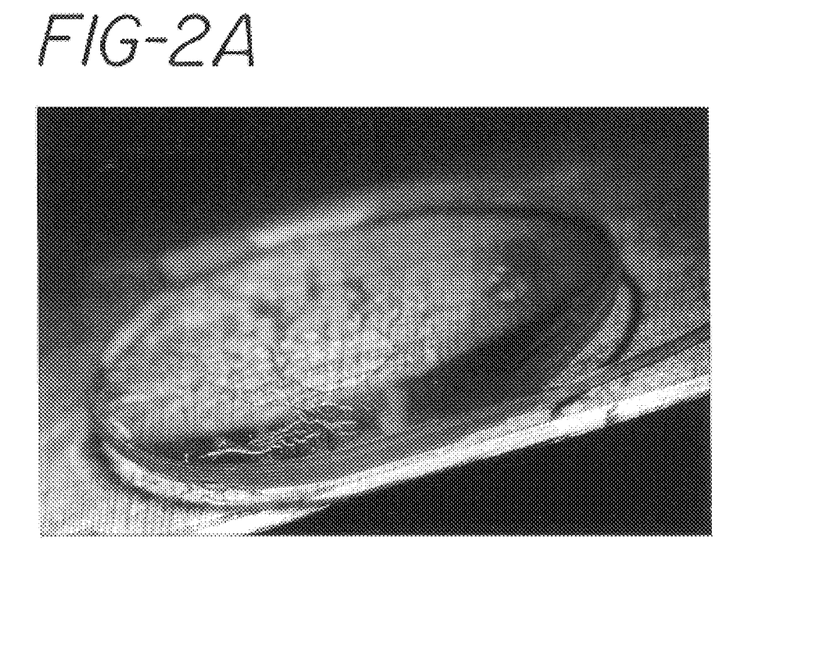
FIG. 2A is a photomicrograph taken at a magnification of 15× showing an overall view in perspective of an intraocular lens within the scope of the invention.

The substantial elimination of glare can be accomplished by adding means onto the edge surface of the lens for reflecting the incident beam of light which contacts this surface away from the retina of the patient. The preferred embodiment for these means is shown in the photomicrographs of the intraocular lens in FIG. 2. In FIG. 2A, there is seen an intraocular lens with a simple, one-piece lens body for focusing visible light on the retina of the patient. The lens body has an integral edge surface defining the circumference of the lens body. Attached to and extending outwardly form the lens body are mutually opposed filamentary haptics. The haptics provide support for the lens in the eye and prevent the lens from decentering after implantation. As clearly depicted in FIG. 2B, the integral edge surface has a plurality of grooves, although it is possible to reflect light away from the retina with a single groove displayed on the edge surface. Each of the grooves is substantially parallel to the other grooves, and each groove extends around the circumference of the lens body in a direction substantially parallel to the plane of the lens body.

Figure 2B:
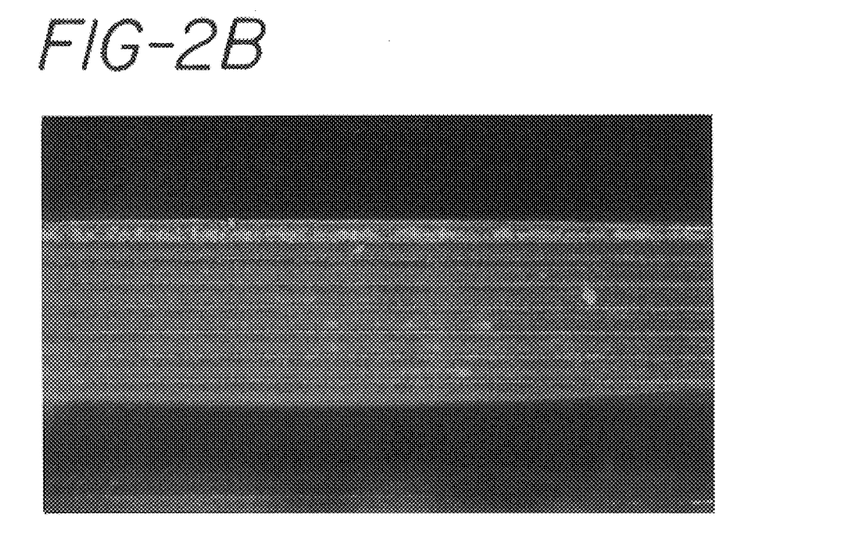
FIG. 2B is a photomicrograph taken at a magnification of 85× showing the edge of the intraocular lens of FIG. 2A.
Figure 3:
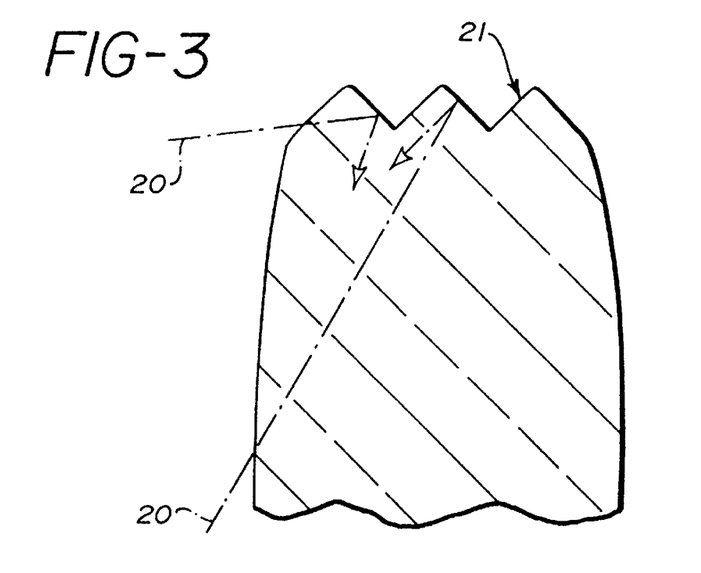
FIG. 3 is an enlarged cross-sectional view of the edge surface of the lens body of an opthalmic lens of this invention, showing the reflecting of an incident beam of light from the edge surface.

Referring now to FIG. 3, there is schematically illustrated the pathway that an off-axis incident beam of light would take when it contacts the edge surface of the intraocular lens photographed in FIGS. 2A and 2B. An incident beam of light 20 would contact the grooved surface 21 of the edge of the lens body, and would reflect away from the retina, thus eliminating or significantly reducing the glare effect.

As depicted in FIG. 3, each of the grooves is preferably a V-shaped groove, although any shape can be used. In actual practice when a V-shaped groove is machined into the edge surface of the lens, and sharp outer edges may be abraded off during processing, e.g. during tumbling to polish the lens, so that the V-shaped groove may actually have somewhat rounded edges. However, this V-shaped configuration is preferred because other configurations, particularly those in which the grooves are essentially round in shape, reduce the effectiveness by allowing more unwanted glare images.

The actual number of grooves added onto the edge surface can vary over a wide range, anywhere from a single groove as previously mentioned to a multiplicity of grooves. The number of grooves is not critical to the practice of this invention, and it will depend on the thickness of the edge surface as well as the width of each groove. Generally, it is preferred to have multiple grooves because as the number of grooves increases the required depth of each groove correspondingly decreases. This is advantageous because if the depth of each groove becomes too large, then there is the possibility that the groove could intrude into the optic zone and consequently affect the visual performance of the lens body. On the other hand, there would reach a point where each individual groove would become too small, which could increase the possibility of unwanted light scattering or diffraction from the edge surface. Advantageously, the number of grooves is such that the depth of each groove varies within a range extending from the wavelength of light to about 400× greater than the wavelength of light (the wavelength of light in the visible spectrum ranges from about 450 to about 750 nanometers). Normally, the exact dimensions of each groove are such that a proper balancing is struck between the optical performance of the lens and manufacturing constraints.

Figure 4:
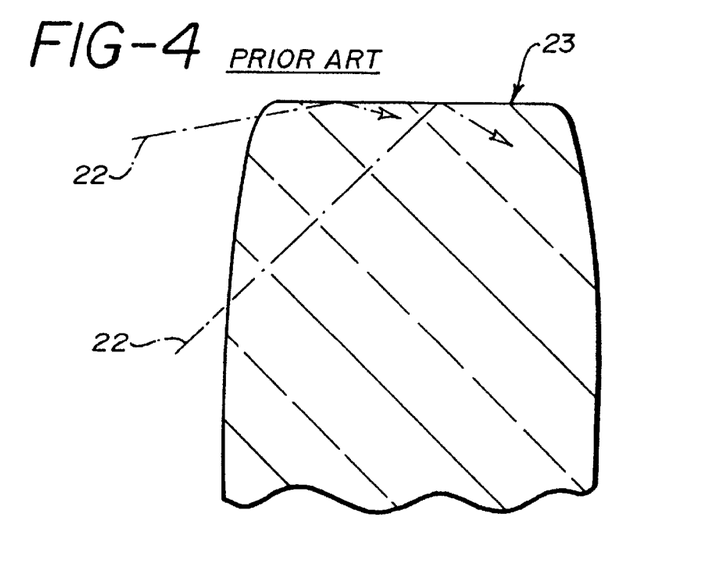
FIG. 4 is an enlarged cross-sectional view of the edge surface of the lens body of a conventional opthalmic lens, showing the reflection of an incident beam of light from the edge surface.

The difference in performance of the grooved-edge lens of FIG. 3 form a conventional flat or rounded-edge lens of the prior art is illustrated in FIG. 4. Here, in FIG. 4, an incident beam of light 22 contacts the flat edge surface 23 of the lens body and it reflects this light toward the retinal surface of the eye. This reflection correspondingly increases the risk of creating unwanted glare on the retina.

Figure 6:
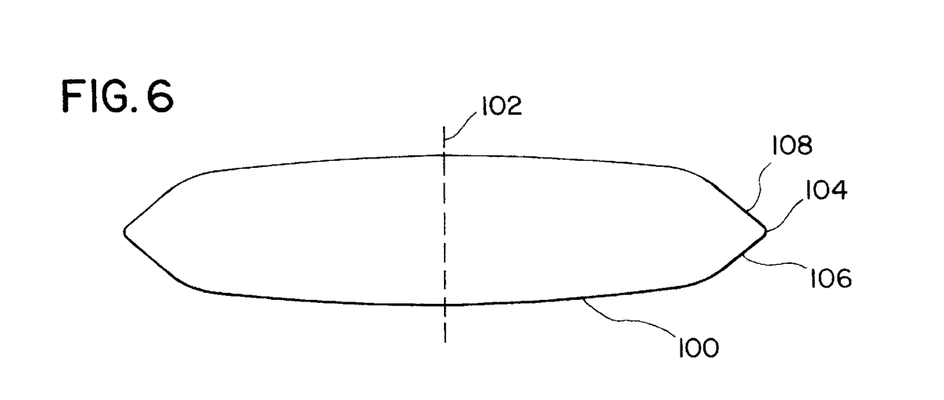
FIG. 6 is cross-sectional view taken along the lens diameter of an alternate embodiment of the invention having beveled portions.

Referring now to FIG. 6, shown is an opthalmic lens body 100 having a normal optical axis 102 incorporating an alternative embodiment of the present invention. The edge surface 104 of the lens body is comprised of at least one posterior beveled portion 106 angled in such a way so as to reflect incident light rays on the edge surface away from the retina. In the instance where the edge contains one beveled portion on the posterior side of the lens, the angle between the beveled portion 106 and the normal optical axis 102 is between about 10° and 45°, with 25° being the preferred angle.

Where this embodiment has two or more beveled portions, the angles between the beveled portions 106, 108 and the normal optical axis 102 is between about 10° and 60°, with 30° being the preferred angle. The included angle between the anterior and posterior beveled portions is preferred to be between about 120° and 160°.

Figure 7:
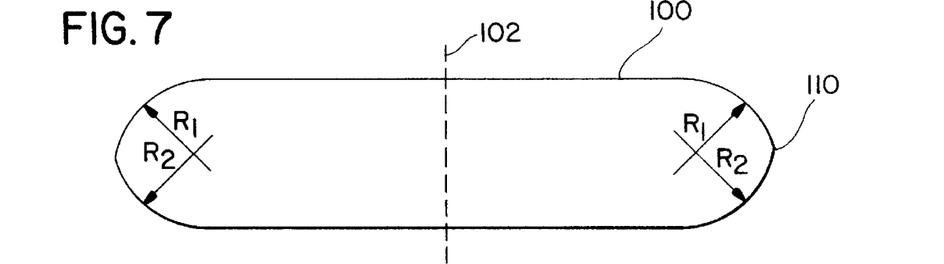
FIG. 7 is a cross-sectional view taken along the lens diameter of another alternate embodiment of the invention having a curved convex edge surface.

Referring now to FIG. 7, shown is an opthalmic lens body 100 having a normal optical axis 102 incorporating the preferred embodiment of the present invention. The edge surface 110 of the lens body is comprised of a convex curved form with a slope at each point angles within the preferred range of angles given above so as to reflect incident light rays on the edge surface away from the retina. One such curved surface has circular radii of curvature $R_1$ and $R_2$ where both are generally defined by the equation:

$$R^2 = x^2 + y^2$$

where R is the radius of curvature, x is the horizontal coordinate and y the vertical coordinate of each point on the curved surface cross section. The radius, R, will range between about ½ and about twice the lens edge thickness, with R about equal to the edge thickness preferred.

The beneficial effects from using the opthalmic lens of this invention are realized to a great degree in one particular instance when the lens body is relatively small. With respect to opthalmic lenses, conventional round lenses typically have diameters between 6–7 mm, but with the advent of small incision surgery, round lenses with diameters less than or equal to 5.5 mm are becoming more common. The reduced diameter of the lens body relative to the pupil creates a correspondingly increased risk that incident light will contact the edge surface of these lens.

Not only is the frequency upon which incident light contacts the edge surface of the lens a determining factor in the severity of unwanted glare problems, but also the thickness of the edge surface tends to accentuate this problem. Unfortunately, as the thickness of the edge increases, the severity of the glare problem tends to increase as well. In this regard, round lenses typically have a thin edge with a thickness between about 0.20 to about 0.28 mm, although edge thicknesses outside this range are possible. However, the ovoid lens typically has a varying thickness at the edge surface, with a thin edge region and a thick edge region. The thickness of the thick edge region will vary depending on the optical power of the lens, but is typically about 0.40 mm for a 20 diopter lens. It is as these regions of increased edge thickness which make the use of a grooved-edge surface, or any other means displayed on the edge surface of the lens body, particularly attractive for reflecting light away from the retina.

The placement of grooves on the edge surface of the lens body of an opthalmic lens can be accomplished using conventional machine methods. For example, a milling machine with a cutter specifically designed to provide the desired grooved edge effect can be used. Alternatively, other methods such as casting or embossing can be used. If the lens is a soft lens such as silicone, soft acrylic, or a hydrogel, then the grooves can be added onto the lens during the molding process. Specifically, this would require simply matching a mold for the lens which has the desired configuration of the grooves.

Figure 8:
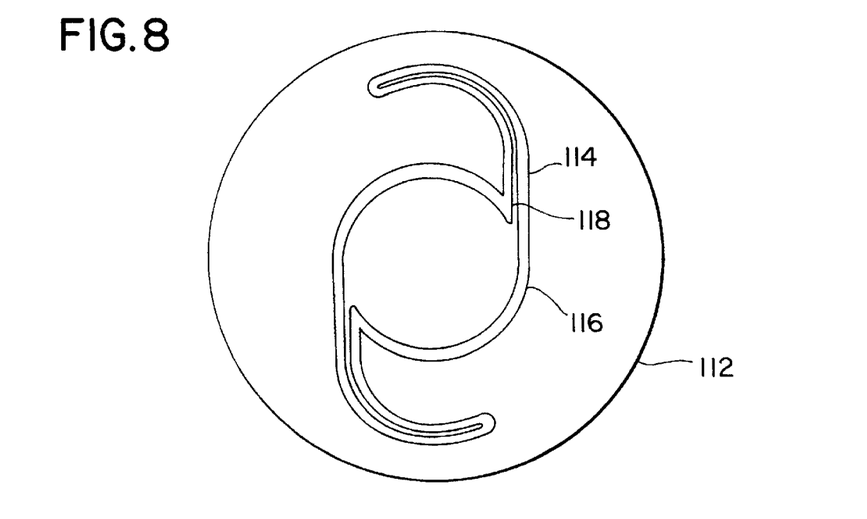
FIG. 8 is a top plan view of a lens blank having cut there from an intraocular lens consisting of the optic and the haptic.

One-piece intraocular lenses are typically made by matching, as is preferred for lenses of the present invention. As shown in FIG. 8, there is lens blank 112 which has been diamond turned on a precision lathe to provide the optical front and back surfaces of the lens. This process is used on prior art lenses and is also applicable to the embodiments of the invention depicted in FIG. 6 and FIG. 7.

Figure 9A:
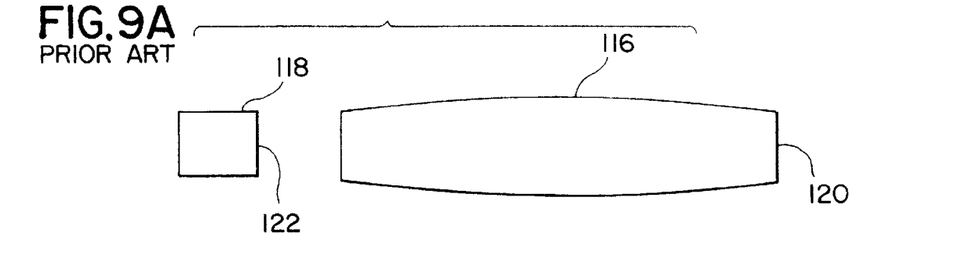
FIGS. 9a and 9b show in cross section the optic and haptic portions of a prior art milled intraocular lens before and after tumble polishing, respectively.

As is conventional in the prior art process, the following steps are also preferred in the present invention. The lens is then transferred to a milling machine where the edge of optic 116 and haptic loops 118 are machined along mill cutter path 114. Referring now to FIG. 9a, in the prior art process this left the edge 120 of optic 116 and the edge 122 of optic 118 flat with sharp corners. In addition to flat edges ont he optic causing glare problems from edge reflections as described above, sharp corners can also cause tissue irritation after the intraocular lens is implanted.

The prior art addressed this problem by employing the process of tumble polishing. Tumble polishing is the placement of the cut and milled lenses into containers of extremely fine abrasive material which serves to both remove the lap marks form the diamond turning of the optical surfaces as well as to round the sharp edges, as seen in FIG. 9b.

Figure 9B:
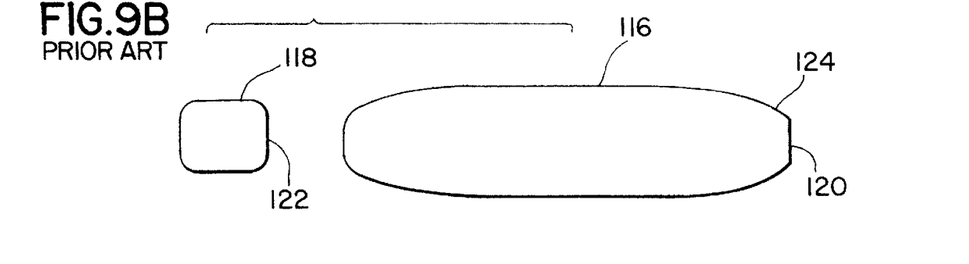

Referring to FIG. 9b, it can be seen that optic 116 has rounded corners 124, but the edge portion 120 is still flat and prone to cause edge glare problems. In addition, the period of tumble polishing required to round the edge of the optic may be up to two weeks. This degree of polishing is not necessary merely to remove the lap marks from the diamond turning of the optical surfaces.

Figure 10:
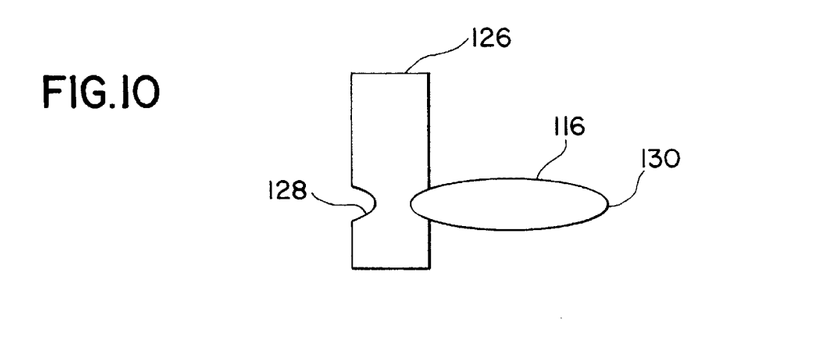
FIG. 10 shows in cross sectional view an alternate embodiment lens being made according to the present invention by a milling tool.

Referring now to FIG. 10, there is shown in addition to the optic portions 116 of the intraocular lens, a form tool milling cutter 126. As can be seen from this Figure, the form tool milling cutter has a concave shape in the cutting portion 128 which corresponds to the convex portion desired ont he edge 130 of a lens made according to the present invention.

Figure 11:
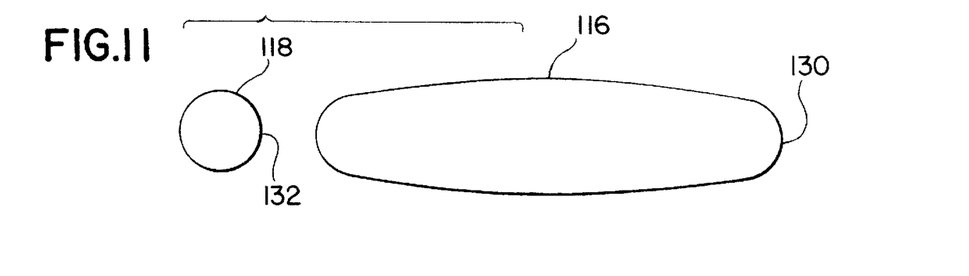
FIG. 11 shows in cross section corresponding to those cross sections of FIG. 9, a view of the optic and haptic portion of an intraocular lens after manufacture is completed by the method of the present invention.

Turning to FIG. 11, the results of the use of such a contoured form tool milling cutter with a concave cutting surface corresponding to that described above is shown. Not only does the optic poriton 116 of the intraocular lens have the appropriately formed convex edge surface 130, but also the haptic portion 118 has an appropriately rounded edge surface 132. While tumble polishing is still required to remove lap marks from the diamond turning of the optical front and back surfaces of the intraocular lens, the tumble polishing time can be significantly reduced. The lens as shown in FIG. 11 will look essentially the same both before and after the amount of tumbling required to remove the microscopic lap lines on the optical surfaces of the intraocular lens.

In addition to producing a curved convex surface such as 110 and 130 found in FIGS. 7 and 11, respectively, a form tool milling cutter may be sued to produce a bevel edge shape corresponding to that of the edge 104 found in the lens of FIG. 6.

Figure 5A:
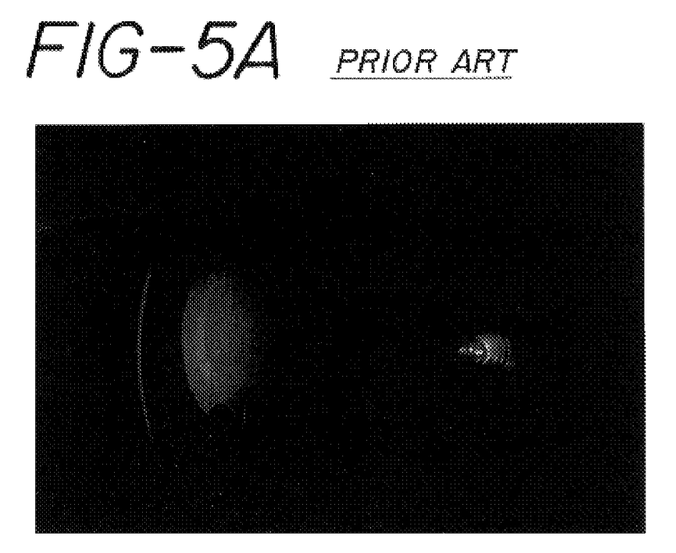
FIG. 5A is a photograph showing the retinal image produced from a conventional intraocular lens implanted in an eye model for simulating optical performance.
Figure 5B:
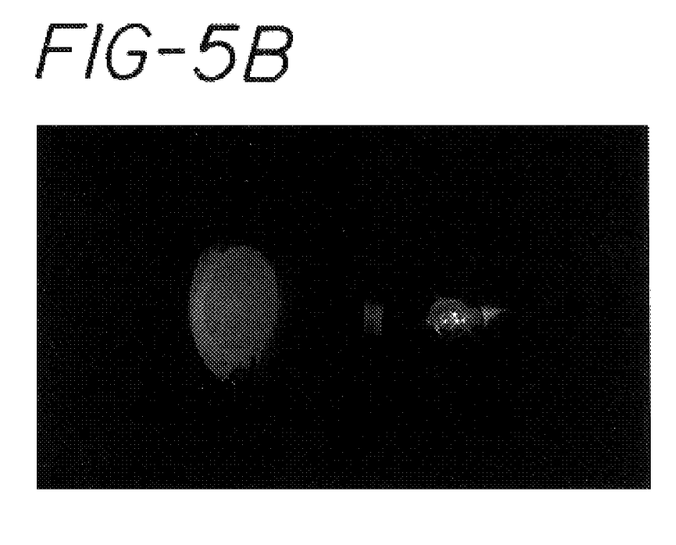
FIG. 5B is a photograph showing the retinal image produced from a intraocular lens within the scope of this invention implanted in the same eye model for simulating optical performance as used for preparing the photograph of FIG. 5A.

Simulating retinal images produced by a conventional round-edge intraocular lens and a grooved-edge intraocular lens are shown in the photographs in FIGS. 5A and 5B to illustrate the differences in the optical performance of these lenses. Sample lenses were tested in a Gullstrand eye model for optical performance. The Gullstrand model is a mechanical simulation of a human eye, using typical eye dimensions. The eye model is made to allow the insertion of test lenses to measure the optical performance of an intraocular lens in place of the natural crystalline lens. The Gullstrand eye model is a conventional eye model described originally in A. Gullstrand, Dei Optisch Abbedung, ed.3, Helmholtz Handbuch der Physilogischen Optik, Hamburg 1909; and then more currently, for example, in H. H. Emsley, Visual Optics, 3rd ed., pg. 346, Butterworths, Scarborough, Ont. 1955. The simulated retinal image is photographed directly to show the images that might be seen by a patient with the test lens implanted.

FIG. 5A is the image from a standard ovoid lens with a conventional edge surface without grooves. FIG. 5B is the image from a grooved ovoid non-glare lens within the scope of this invention. The solid circular portion shown in each of the photographs is the useful image from light passing through the lens. The crescent to the left of the useful image for the non-grooved intraocular lens is the unwanted image from edge reflection.

A comparison of the photographs shown in FIGS. 5A and 5B illustrates that the crescent-shaped image produced from edge reflection in FIG. 5A is dramatically eliminated in the photograph shown in FIG. 5B. Therefore, these experimental results show that unwanted optical images caused by reflections from the edges of intraocular lenses, as well as any other kind of opthalmic lens, can be eliminated by the addition of means on the edge surface for reflecting light away from the retina, most particularly by the addition of V-shaped grooves on the edge surface.

This invention has been described in its preferred embodiments. Numerous additional embedments within the scope and spirit of this invention can be readily envisioned by those skilled in the art, after having the benefit of reading this specification.

We claim:

1. An opthalmic lens for focusing visible light on a retina of a patient, said lens comprising a lens body having two optical surfaces joined by a third, integral edge surface formed between said two optical surfaces so as to not extend anteriorly or posteriorly beyond said two optical surfaces, and to define a circumference of said lens body and a normal optical axis to the lens body, said integral edge surface comprising at least two beveled portions continuous around said circumference of said lens body configured to reflect visible light incident on said integral edge surface away from the retina.

2. The lens of claim 1 wherein said at least two beveled portions comprise a posterior beveled portion and an anterior beveled portion.

3. The lens of claim 2 wherein said anterior and posterior beveled portions are at an angle of between approximately 10° and 60° to the normal optical axis of said lens body.

4. The lens of claim 3 wherein said anterior and posterior beveled portions are at an angle of approximately 30° to the normal optical axis of said lens body.

5. The lens of claim 3 wherein said anterior and posterior beveled portions form an included angle of between approximately 120° and 160°.

6. An opthalmic lens for focusing visible light on a retina of a patient, said lens comprising a lens body having two optical surfaces joined by a third, integral edge surface with an edge thickness formed between said two optical surfaces so as to not extend anteriorly or posteriorly beyond said two optical surfaces, and to define a circumference of said lens body and a normal optical axis to the lens body, said integral edge surface being a third optical surface comprising at least two beveled portions continuous around said circumference of said lens body oriented to reflect visible light which is incident on said edge surface away from the retina.

7. The lens of claim 6 wherein said at least two beveled portions comprise a posterior beveled portion and an anterior beveled portion.

8. The lens of claim 7 wherein said anterior and posterior beveled portions are at an angle of between about 10° and 60° to the normal optical axis of said lens body.

9. The lens of claim 8 wherein said anterior and posterior beveled portions are at an angle of about 30° to the normal optical axis of said lens body.

10. The lens of claim 8 wherein said anterior and posterior beveled portions from an included angle of between about 120° and 160°.

11. A method for focusing visible light on a retina of an eye while preventing unwanted optical images from being formed on the retina, comprising:

positioning a lens body in the path of visible light to the eye, the lens body having two optical surfaces joined by a third, peripheral, integral edge surface with an edge thickness defining a circumference of said lens body, the integral edge surface being a third optical surface having at least two beveled portions continuous around said circumference of said lens body;

focusing light which passes through the two optical surfaces onto the retina; and reflecting light which is incident on the third optical surface away from the retina.

\* \* \* \* \*